(12) United States Patent
Okamura et al.

(10) Patent No.: US 6,861,235 B1
(45) Date of Patent: Mar. 1, 2005

(54) METHOD FOR CONTROLLING TARGET MICROORGANISM

(75) Inventors: Yukio Okamura, Shizuoka-ken (JP); Naoki Murakami, Toyota (JP); Wakana Yagi, Aichi-ken (JP)

(73) Assignee: Toyota Jidosha Kabushiki Kaisha, Toyota (JP)

( * ) Notice: Subject to any disclaimer, the term of this patent is extended or adjusted under 35 U.S.C. 154(b) by 0 days.

(21) Appl. No.: 09/623,196

(22) PCT Filed: Mar. 5, 1999

(86) PCT No.: PCT/JP99/01086

§ 371 (c)(1), (2), (4) Date: Aug. 29, 2000

(87) PCT Pub. No.: WO99/44422

PCT Pub. Date: Sep. 10, 1999

(30) Foreign Application Priority Data

Mar. 6, 1998 (JP) ............................................ 10-055169
May 27, 1998 (JP) ............................................ 10-145708

(51) Int. Cl.$^7$ ............................ C12Q 1/02; C12N 1/02; C12N 1/20; B09B 3/00
(52) U.S. Cl. ........................ 435/29; 435/261; 435/262; 435/264; 435/821; 435/822
(58) Field of Search .......................... 435/29, 261, 262, 435/264, 821, 822

(56) References Cited

U.S. PATENT DOCUMENTS

| | | | |
|---|---|---|---|
| 5,508,193 A | * 4/1996 | Mandelbaum et al. ... | 435/253.3 |
| 5,653,675 A | * 8/1997 | Kanno et al. ................ | 588/249 |
| 5,789,191 A | 8/1998 | Mayer et al. .................. | 435/35 |
| 5,998,198 A | * 12/1999 | Nakayama et al. ....... | 435/262.5 |

FOREIGN PATENT DOCUMENTS

| | | |
|---|---|---|
| DE | 37 23 447 A1 | 10/1988 |
| JP | 61-263902 | 11/1986 |
| JP | 4-502277 | 4/1992 |
| JP | 7-88465 | 4/1995 |
| JP | 9-4816 | 1/1997 |
| JP | 9-501835 | 2/1997 |
| JP | 9-100189 | 4/1997 |
| JP | 10-52259 | 2/1998 |
| WO | 95/06133 | 3/1995 |

OTHER PUBLICATIONS

Merriam–Webster' Collegiate Dictionary. 10th ed. 1996. p. 249.*
ATCC Catalogue. ATCC Bacteria and Bacteriophages. 19 edition. 1996. pp.78–80.*
Schaad et al. Inetrnational Journal of Systematic Bacteriology. 1978. vol. 28, No. 1, pp. 117–125.*
Sandin et al. Antimicrobial Agents and Chemotherapy. 1990. vol. 34, No. 3, pp. 491–493.*
ATCC webpage titled "ATCC. Search Catalogues" retrived on May 9, 2001 from website http://phage.atcc.org./cgi–bin/searching.*
Russian Office Action dated Dec. 25, 2002 in a corresponding Russian Application 2000I25559/13(027409) filed Jun. 10, 2000, Related to PCT99/01086.
A.K. Troufanova. Microbiological Processes on Soils and Farm Cultures Productivity, "The State of Phytopathogenic Fungi on Soils Depending on Bacterial Flora," pp. 362–365 (1986)(with partial English translation).
"Dictionary of Plant Physiology," edited by the Phytopathological Society of Japan, Yokendo, 1995, pp. 701–705.
"New Soil Microorganisms," published by Hakuyusha Corp., 1997, pp. 128–131.

* cited by examiner

*Primary Examiner*—Vera Afremova
(74) *Attorney, Agent, or Firm*—Burns, Doane, Swecker & Mathis, L.L.P.

(57) ABSTRACT

There is provided a method for controlling a target microorganism characterized in that an extrinsic environmental factor is added to a culture system where said target microorganism and other microbes coexist, said extrinsic environmental factor providing a desirable growth condition for the other microorganisms but an undesirable growth condition for the target microorganism, and said extrinsic environmental factor is typically an organic substance that is assimilable by the above other microorganisms but not by the target microorganism, and includes a sugar, an amino acid, an alkanol amine, an organic acid, and the like. In particular, the target microorganism is N16-1 strain of *Burkholderia* (FERM BP-5504) and the substance is D-serine.

3 Claims, 11 Drawing Sheets

Fig.1
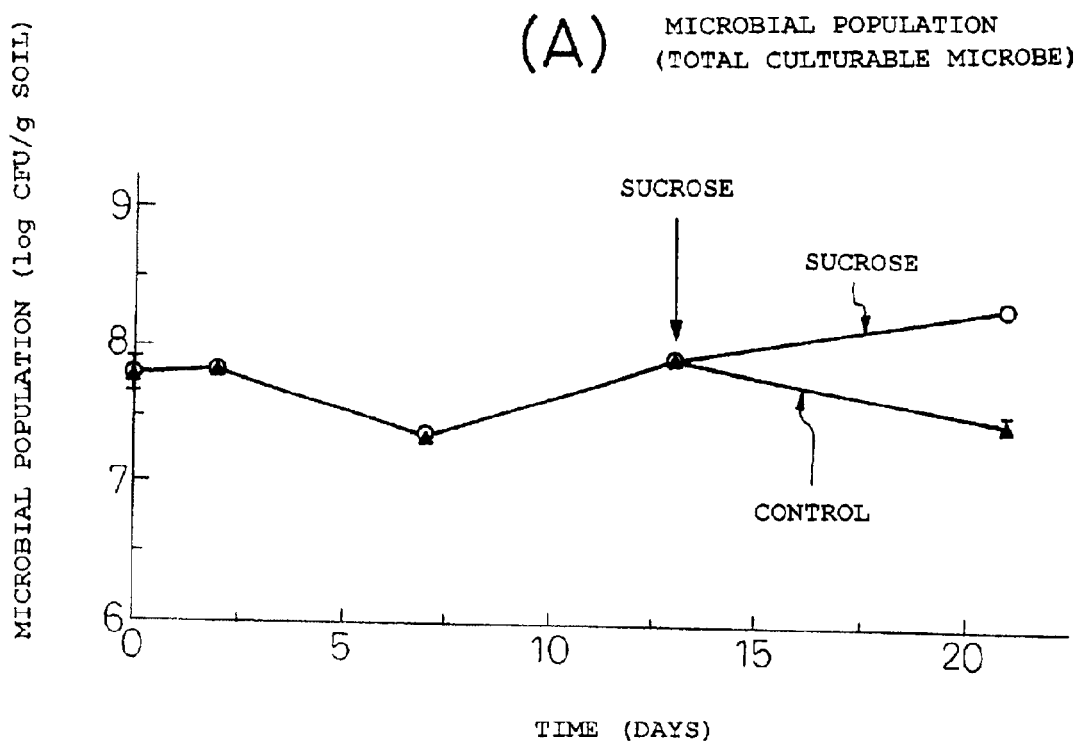
(A) MICROBIAL POPULATION (TOTAL CULTURABLE MICROBE)
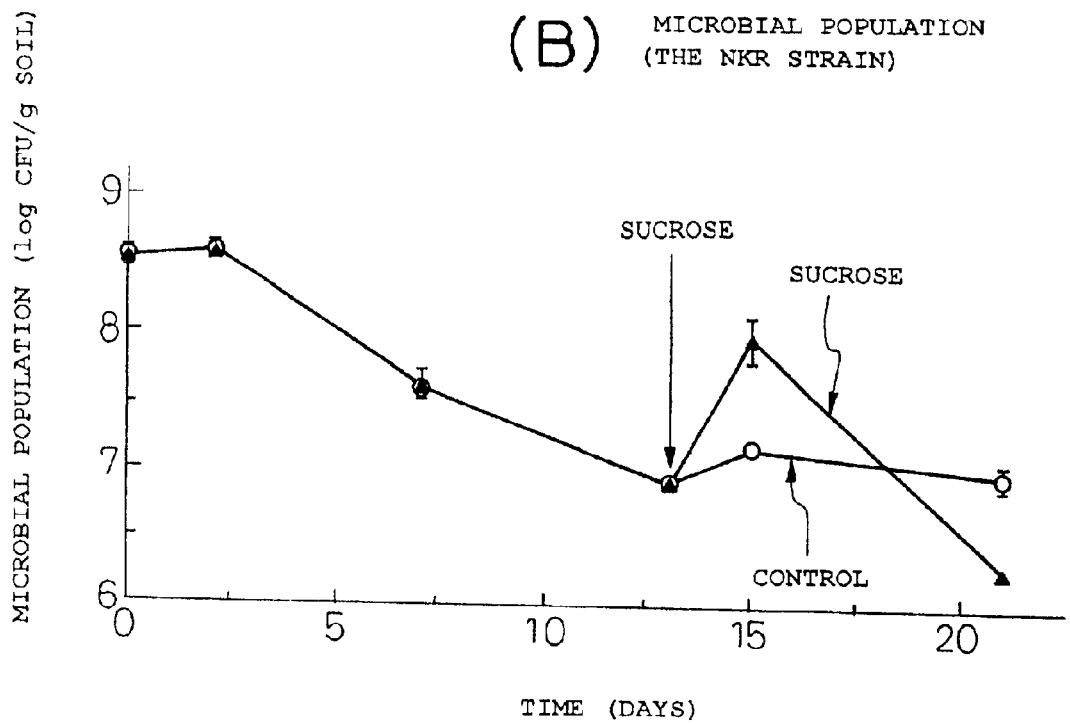
(B) MICROBIAL POPULATION (THE NKR STRAIN)

A  B  C  D

METHOD FOR CONTROLLING TARGET MICROORGANISM

TECHNICAL FIELD

The present invention relates to processes for controlling the growth of specific target microorganisms and, more preferably, processes for controlling the growth of a microorganism artificially added after purification treatment, by microbial purification of contaminated soils, and thereby recovering the indigenous microbial flora. The present invention also relates to processes for controlling pathogenic microorganisms in soil contaminated by said pathogenic microorganisms.

BACKGROUND ART

In recent years, much attention has been focused on bioremediation as a technology for the purification of contaminated soils. In bioremediation, contaminant-decomposing microorganisms (target microorganisms) that occur naturally are allowed to grow and the grown microorganisms are applied to the soil. Though soils can be purified by this method, many contaminant-decomposing microorganisms can remain in the soil, which is not desirable in terms of the balance of the soil ecosystem. Thus, as methods for removing contaminant-decomposing microorganisms that remain after the treatment, there are known methods such as gene recombinant technology that employs a suicide system (suicide gene) (Manual for Introduction of Recombinants into the Ecosystem, 1993, Ministry of Agriculture, Forestry, and Fisheries, P36–47), chemical and physical sterilization methods (Dictionary of Plant Physiology, edited by The Phytopathological society of Japan, Yokendo, 1995, pp. 701–719), and methods of imparting auxotrophic properties to target organisms.

However, each of these methods has its own problems. For example, since the method of using suicide system is based on recombinant technology it is not suitable for use in the field (an open system), and it usefulness is uncertain. The chemical and physical sterilization methods have drawbacks that all microorganisms including the soil microorganisms become the target of sterilization, and therefore may disturb the ecosystem. And, in the use of auxotrophic microorganisms, there is a risk that auxotrophy may disappear due to reverse mutation.

THE DISCLOSURE OF THE INVENTION

Therefore, it is an object of the present invention to provide a novel method that permits the restoration of the indigenous microbial flora in the soil, said method being free from the drawbacks the conventional methods have.

In order to solve the above problems, the present invention generally provides a method for controlling target microorganisms characterized in that an extrinsic environmental factor is added to a culture system where said target microorganisms and other microbes coexist, said extrinsic environmental factor providing a desirable growth condition for the other microorganisms but an undesirable growth condition for the target microorganisms.

The above extrinsic environmental factor is an organic substance that can be assimilated by the above other microorganisms, but not by the target microorganisms. Preferably the organic substances are simple compounds such as sugar, amino acids, lower alkanol amines, and organic acids. The organic substances depends on the target microorganisms. When, for example, it is a microorganism of the genus *Burkholderia*, strain N16-1, said organic compound is preferably an amino acid, D-serine. When it is *Ralstonea solanacearum*, said organic compound is preferably D-serine serine or ethanolamine.

The term "target microorganism" as used herein means that it is a contaminant-degrading microorganism or a pathogenic bacterium.

BRIEF DESCRIPTION OF THE DRAWINGS

FIG. 1 is a graph showing the controlling effect of sucrose on the growth of the NKR strain in the soil.

EMBODIMENT FOR CARRYING OUT THE INVENTION

Figure 2:
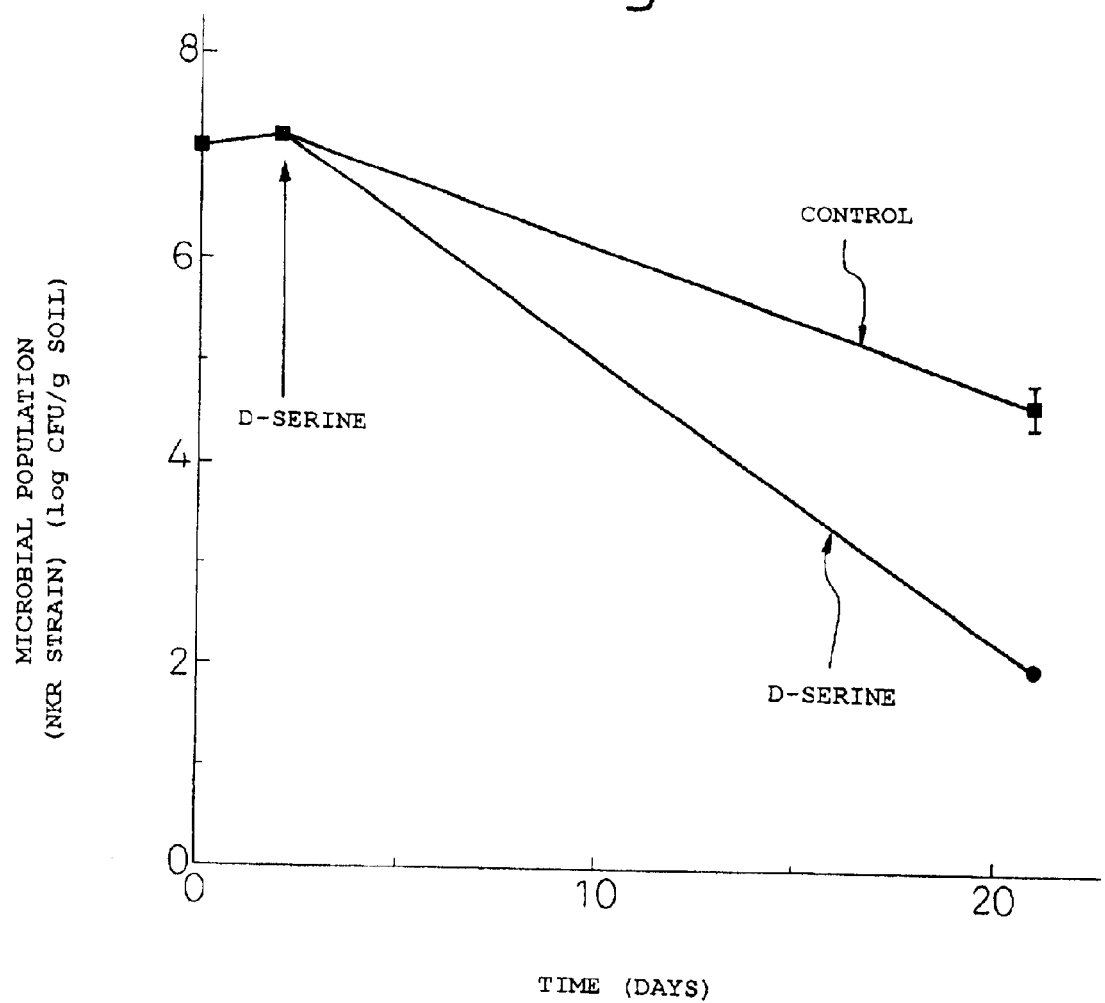
FIG. 2 is a graph showing the controlling effect of D-serine on the growth of the NKR strain in the soil.

The present invention is generally used to promote the growth of other microorganisms while controlling the growth of a particular microbe in a system where a plurality of microorganisms are present, and is typically used to restore the natural microbial system after the treatment of a contaminated soil by bioremediation. Alternatively, the present invention is used to purify the soils contaminated by pathogenic microorganisms. Thus, for the purpose of purifying soils contaminated by contaminants, bioremediation involves the inoculation of microorganisms capable of assimilating and/or degrading the contaminants to the soil to be treated thereby to degrade and eliminate the contaminants in the soil. Accordingly, after the treatment of the soil is finished, the contaminant-degrading microorganisms artificially added to the soil may become established therein. After the treatment of contaminated soils, therefore, it is necessary to control the growth of the microorganism used for the treatment and to restore the indigenous microbial flora. Alternatively, if plant pathogenic microbes developed or increased in number in farmlands etc., it is necessary to control said pathogens while maintaining the indigenous microbial flora.

Thus, according to the method of the present invention, an organic substance that is not assimilated by contaminant-degrading microbes but is assimilated by the indigenous microorganisms is added to the soil that underwent purification treatment. This will promote the growth of the indigenous microorganisms, with a result that the growth of contaminant-degrading microorganisms is controlled and they are eliminated from the soil. Alternatively, the growth of pathogens that have developed or propagated are controlled and they are eliminated.

The method of the present invention can be used in the treatment of soils contaminated by contaminants including, for example, organochlorine compounds such as trichloroethylene (TCE) and dichloroethylene, petroleum hydrocarbons such as phenol and heavy oil, agricultural chemicals such as 2,4-D (2,4-dichlorophenoxy acetate) and pantachlorophenol. For the treatment of these contaminants, fungi such as white rot microbes, bacteria such as the genus *Burkholderia* and the genus *Pseudomonas*, and other bacteria may be used. Alternatively, they can be used for the treatment of the soil in which pathogenic microbes have developed or increased in number. The type of organic compounds that are not assimilated by the target microorganisms but are assimilated by the indigenous microorganisms differs with the type of the target microorganisms and can be experimentally selected based on the disclosure of the present invention. Whether a specific microorganism can assimilate an organic substance or not can be determined by commonly used microbiological testing methods.

For example, it can be tested by inoculating a microorganism to a solid medium or a liquid medium containing the test organic compound as a sole carbon or nitrogen source, and then observing the development of colonies or the density of the medium. Alternatively, a test organic compound is added to a medium containing an oxidation-reduction indicator, in which medium a test microorganism is cultured and its assimilative property can be determined based on the presence of the development or intensity of color in the medium by the oxidation-reduction indicator.

However, those organic compounds that are not assimilated by the target microorganisms but are assimilated by the indigenous microorganisms cannot always be used in the present invention. For example, even those organic substances that cannot be assimilated by contaminant-degrading microorganisms or plant pathogenic microorganisms may promote the growth of said microorganisms if they are degraded by indigenous microorganisms and the degraded products or dead indigenous microorganisms are assimilated by the contaminant-degrading microorganisms or the pathogens. In such cases, if the growth promotion of contaminant-degrading microorganisms or pathogenic microorganisms by degraded products is permanent instead of transient, which is more preferable, they are not suitable as organic substances for the purpose of the present invention.

Thus, it is necessary to select (primary screening) candidate organic compounds by an assimilation test, using a specific contaminant-degrading microorganism or pathogenic microorganism, and then to test (secondary screening) whether they are actually useful for the purpose of the present invention. This test can also be easily carried out according to the disclosure of the present invention. For example, a specific soil that is to be a subject of degradation is collected, to which a test organic compound is added at a concentration of a few hundred ppm to a few thousand ppm. A test microorganism (contaminant-degrading microorganism or pathogenic microorganism) is inoculated to the soil, which is then incubated at room temperature. The number of test microorganisms may be counted over time or after incubation for a certain period of time to select those organic substances that caused reduction in the number of the contaminant-degrading microorganisms or the pathogenic microorganisms, which can be carried out based on the disclosure of the present invention.

In the above test, it is necessary to differentially count the number of the contaminant-degrading microorganisms or the pathogenic microorganisms in the soil, which can be carried out by using a medium that permits selective counting of the test microorganisms. This can be easily carried out by rendering the contaminant-degrading microorganisms or the pathogenic microorganisms drug-resistant, for example antibiotic-resistant. For example, by imparting to contaminant-degrading microorganisms resistance against antibiotics which common indigenous microorganisms do not have, and culturing soil samples on a solid medium containing said antibiotics and a solid medium containing no antibiotics, contaminant-degrading microorganisms can only form colonies (or large colonies) on the solid medium containing the antibiotics, so that by determining the numbers of the colonies the number of microorganisms can be differentially counted.

Then, for the purpose of screening the organic substances of the present invention, imparting to contaminant-degrading microorganisms drug-resistance, for example resistance against antibiotics, can be carried out relatively easily based on a conventional method. For example, a drug-resistant gene can be introduced by the introduction of a plasmid or a transposon. Alternatively, contaminant-degrading microorganisms are cultured in, for example, a liquid medium containing an antibiotic, and the microorganisms that propagated are cultured in a medium containing a higher concentration of the antibiotic, thus repeating such enrichment subculturing for a plurality of times. Alternatively, contaminant-degrading microorganisms are cultured on a solid medium containing a certain concentration of antibiotics to allow the microorganisms to form colonies, which colonies are then cultured on a solid medium containing a higher concentration of the antibiotics to allow the microorganisms to form colonies, thus repeating this a plurality of times.

As the above extrinsic environmental factor, there can be preferably mentioned sugars, amino acids, lower alkanolamines, organic acids and the like. As a sugar, sucrose is preferred. As an amino acid, D-amino acids are preferred, and for example D-serine, D-alanine, D-cysteine, or the like is used. As a lower alkanolamine, there can be mentioned an amine of an alkanol having 1–5 carbons, such as ethanolamine. As an organic acid, there can be mentioned an alkanoic acid, hydroxyalkanoic acid, keto acid or the like having about 1–6 carbons, such as pyruvic acid.

By way of a specific example for use in the present invention, a microorganism of the genus *Burkholderia* may be mentioned as a microorganism to be used for bioremediation of the soil contaminated by trichloroethylene. As a *Burkholderia* microorganism, there can be mentioned the N16-1 strain (FERM BP-5504) and the like. The microorganism is specifically described in Japanese Patent Application No. 9-04816, and has been deposited with the National Institute of Bioscience and Human Technology, Agency of Industrial Science and Technology under the above accession number (National Institute of Advanced Industrial Science and Technology, AIST Tsukuba Central 6, 1—1, Higashi 1-Chome, Tsukuba-shi, lbaraki-ken, 305-8566, Japan).

*Burkholderia* sp. N16-1 strain (FERM BP-5504) is, as described in Example 2, does not assimilate various organic compounds including sucrose as a sugar, D-serine as an amino acid and the like. When sucrose among them is added as shown in Example 3, the N16-1 strain is transiently increased but then starts to decline and the indigenous microorganisms become dominant. Although the reason for this is not clearly understood, it is assumed that sucrose is metabolized by the indigenous microorganisms and the metabolites thereof are assimilated by the N16-1 strain, which metabolites transiently enhance the growth of the N16-1 strain.

When a contaminant-degrading microorganism is a microorganism of the genus *Burkholderia*, in particular the N16-1 strain thereof, as shown in Example 4, D-serine is preferred as an organic compound of the present invention. By adding D-serine the cell count of the N16-1 strain becomes markedly reduced as compared to no addition (control).

In practicing the method of the present invention, for example, contaminant-degrading microorganisms are inoculated to the contaminated soil to treat the soil, and after the contaminants are degraded, the organic compound of the present invention, for example D-serine, may be added. Alternatively, the organic compound of the present invention, for example D-serine, may be added to a soil contaminated by pathogenic microorganisms. Though the amount of the organic compound to be added depends on the type of the contaminant-degrading microorganism or the pathogenic microorganism, it is about a few dozen ppm to a few dozen thousand ppm, preferably 100 ppm to 10000 ppm, and more preferably 500 to 5000 ppm. The organic substance may be added at one time, or it may be added in a divided portion for a plurality of times. The time period required to control the number of target microorganisms is usually 1–4 weeks.

EXAMPLES

The present invention will now be explained, in more detail, with reference to the following examples.

Example 1

Improvement of the Strain for Cell Counting (Imparting of Rifampicin-Resistance to the NK1611 Strain)

For the purpose of specific and accurate counting of the cells of the N16-1 strain in the soil, the inventors have developed an accurate counting method that combines a mutant NK1611 strain in which a kanamycin-resistant gene has been introduced, a selection medium (the 1/3 LB (LB manufactured by Difco was diluted 1/3) agar medium to which are added 50 ppm kanamycin and 100 ppm cycloheximide) of this strain, and the Direct Colony PCR method targeting the kanamycin-resistant gene (Japanese Patent Application No. 9-236452). In this method, the Direct Colony PCR method must be performed since the indigenous microorganisms can contaminate the counting when a selection medium alone is used.

In order to conduct simpler cell counting in the present invention, natural mutation was used to impart rifampicin-resistance to the NK1611 strain. Thus, the NK1611 strain was plated on the 1/3 LB agar medium (1.5% agar) to which are added 50 ppm rifampicin, 50 ppm kanamycin, and 100 ppm cycloheximide, which was cultured at 30° C. A natural rifampicin-resistant mutant that developed was cultured in a liquid medium of said medium, and then plated again on the same agar medium having rifampicin at 200 ppm. Well grown colonies were picked up, and single colony isolation was repeated several times to obtain a 50 ppm rifampicin-resistant mutant. The strain was designated as the NKR strain.

Example 2

Evaluation of the Ability of Assimilating Various Carbon Sources by the NKR Strain (Search for Antagonistic Substrates)

A search was performed for carbon sources that cannot be assimilated by the NKR strain. The NKR strain was inoculated to the Biolog GN plate (Biolog) to investigate its assimilation ability for 95 carbon sources. Substrates for which no assimilation (no color development of an oxidation-reduction indicator) was observed were selected. Furthermore, their growth was confirmed in an inorganic salt medium containing 0.5% carbon source. Furthermore, sodium glutamate, sodium tartarate, and sodium succinate, that are not included in the Biolog GN plate, were similarly evaluated.

As a result, compounds for which no color development (compounds that are not assimilated) was observed and compounds for which slight color development (shown in parentheses) was observed are: α-cyclodexrin, dextrin, glycogen, (cellobiose), erythritol, gentiobiose (α-D-lactose), maltose, β-methyl-D-glucose, (D-piscose), D-raffinose, sucrose, (D-trehalose), turanose, xylitol, monomethylsuccinate, acetic acid, (α-hydroxybutyric acid), γ-hydroxybutyric acid, itaconic acid, (α-ketobutyric acid), (α-ketoglutaric acid), (malonic acid), propionic acid, (quininic acid), (D-saccharic acid), (sebacic acid), (glucuronamide), (alanine amide), D-alanine, (L-aspartic acid), glycyl-L-aspartic acid, (L-omithine), D-serine, (L-serine), (L-threonine), (urocanic acid), (uridine), thymidine, phenylethylamine, (putrescine), (2-aminoethanol), 2,3-butanediol, D, L-α-glycerol phosphate, glucose-1-phosphate, and (glucose-6-phosphate).

Example 3

Effects of Sucrose Addition

Five g of the SB soil (adjusted to pH 7.0) was placed to a 50 ml Corning centrifuge tube, and a suspension of the NKR strain cells in water was inoculated therein. Change with time of the cell count was studied using a 1/3 LB agar medium (Difco LB was diluted 1/3, 1.5% agar) to which were added 50 ppm rifampicin, 50 ppm kanamycin and 100 ppm cycloheximide. Change in total cell counts was also studied using a DNB (Eiken's NB was diluted 1/100) agar medium (1.5% agar). After culturing until the NKR strain was established (the cell count becomes constant) in the soil, 500 µl of a solution containing 150 µl of sterile water, 100 µl of a 5×(5-fold strength) M9 medium, and 250 µl of a 10% sucrose solution was added to effect the treatment of cell count control.

The SB soil is a sandy developed earth, and its particle-size distribution is gravel (2–75 mm) 2%, sand (75 µm–2 mm) 80%, silt (5–75 µm) 13%, and clay (less than 5 µm) 5%. pH is 6.5, and the total carbon content in the soil is 0.06%, the content of exchangeable cation (CEC) is 2.6 me/100 g, and the density is 2.614 g/cm³.

The total cell count and the cell count of the NKR strain in the soil were measured by colony formation. Though the NKR strain can grow in a medium containing 200 ppm of rifampicin, no resistant indigenous strains develop in even the SB soil containing 50 ppm rifampicin, and thus in the present example, a medium to which 50 ppm rifampicin was added was used.

The result is shown in FIG. 1. The NKR strain was established at a level of $10^7$ CFU/g soil on day 13 after inoculation. When a cell count control treatment was performed at this time, increases in the total cell counts were observed by the addition of the N, P, and C source. On the other hand, the NKR strain, after a transient increase, decreased slightly.

Example 4

Effect of D-Serine Addition

After inoculating the NKR strain to the pH-adjusted SB soil, it was cultured at 30° C. for 2 days, to which 250 μl of a 10% substrate solution and 350 μl of sterile water were added to attain a cell count control treatment by the addition of 0.5% D-serine. In the case where no serine was added, 100 μl of sterile water was added.

As shown in FIG. 2, when D-serine was added, the cell count of the NKR strain markedly declined as compared to when no D-serine was added. This is because the D-serine addition test was started before the NKR strain was established in the soil. As shown in FIG. 1, the NKR strain significantly reduces the cell count before it is established in the soil.

The above result indicates that D-serine is very effective for the control of the NKR strain in the soil.

The formal name of D-serine is 2-amino-3-hydroxypropionic acid, which is contained in organisms and is also used as a food additive, and which is considered to be a very easy substance to use when the introduction into the soil environment is planned.

Example 5

Effect of L-Serine Addition

Ten g of a pH-adjusted SB soil was placed into a 50 ml Corning centrifuge tube, to which the NKR strain was inoculated. After counting the cell count of the NKR strain and the total cell count, it was cultured at 20° C. for 5 days. Then 0.5 ml of each solution prepared by adding D-serine, L-serine, or DL-serine (the ratio of the D form to the L form is 50:50) to the soil to a concentration of 5000 ppm was added thereto. In the case where no serine was added, 0.1 ml of sterile water was added.

Figure 3:
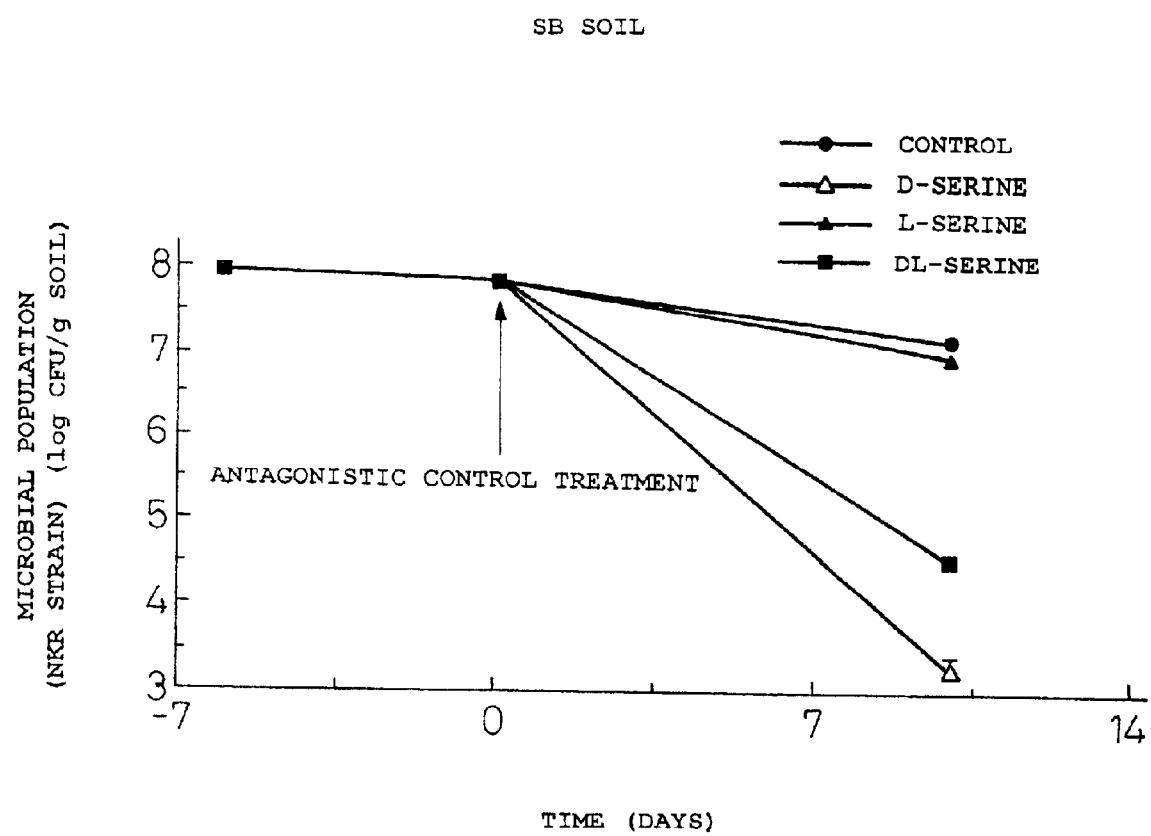
FIG. 3 is a graph showing a comparison of the growth controlling effects of sucrose and D-serine.

When D-serine was added, as shown in FIG. 3, the cell count of the NKR strain markedly declined as compared to when no D-serine was added as in Example 4. However, when L-serine was added, the cell count of the NKR strain remained almost constant as when no L-serine was added. Furthermore, when DL-serine was added, the effect of cell count control can be observed though the degree of reduction is small (FIG. 3).

Example 6

After inoculating the NKR strain at $10^7$ cfu/g wet soil to 10 g of Kuroboku (black) soil A (field soil), Kuroboku (black) soil B (developed land soil), sandy soil A (developed land soil), sandy soil B (developed land soil), sandy soil C (developed land soil), or sandy soil D (grassland non-rhizosphere soil), 500 μl of a 10% D-serine solution was added (to a final concentration of 5000 ppm). As a control, 500 μl of sterile water was added to each soil inoculated with the microorganism.

Figure 4:
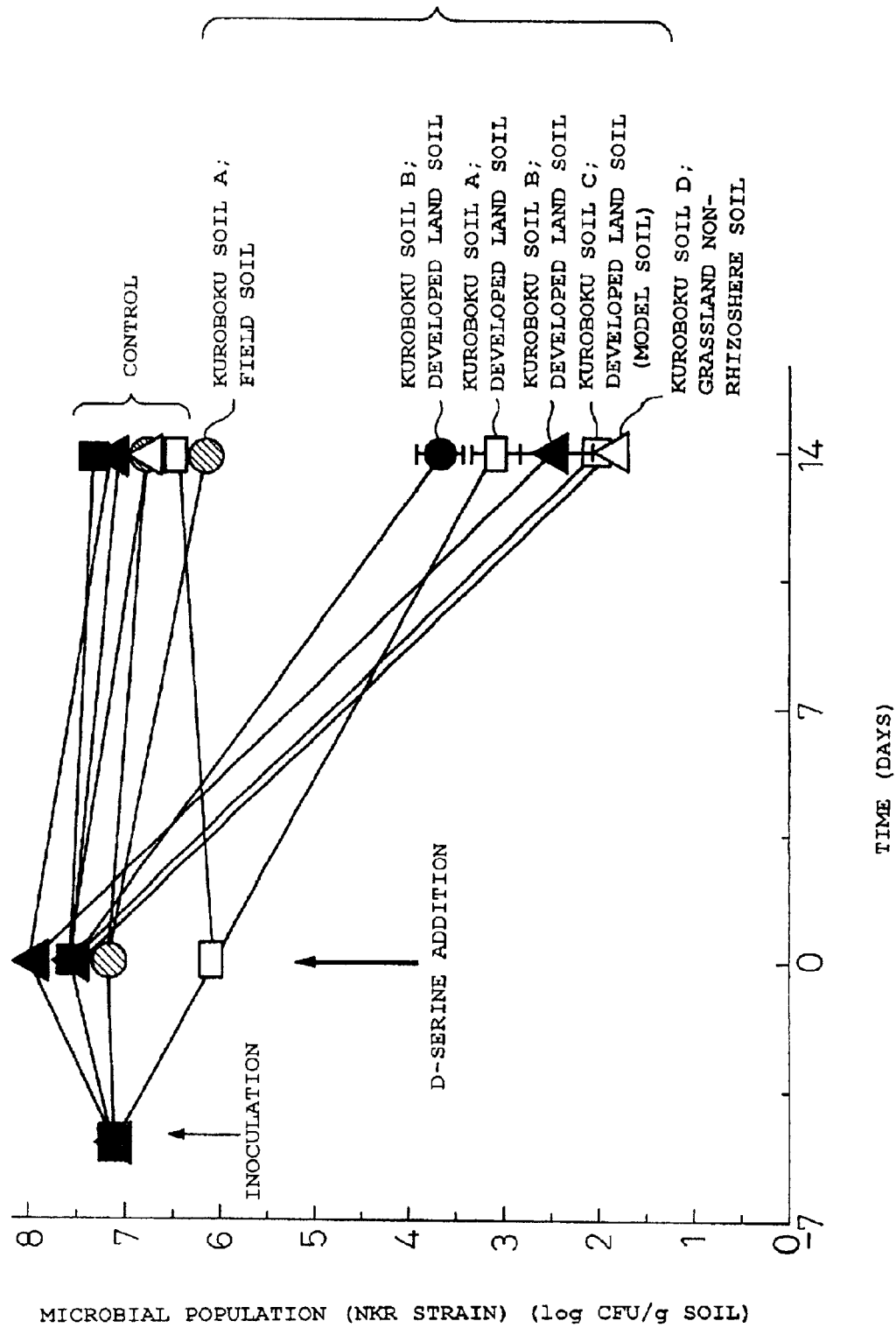
FIG. 4 is a graph showing the controlling effect of D-serine on the growth of the NKR strain in different soils.

As shown in FIG. 4, in all soils excluding Kuroboku (black) soil A, the cell count of the NKR strain markedly declined as compared to the control section, demonstrating the control effect.

Kuroboku (black) soil A is a typical Kuroboku (black) soil and adsorbs organic matter more strongly than Kuroboku (black) B and the microbial flora thereof is characteristic, so that, it is thought, no effects were observed.

Example 7

After inoculating the NKR strain at $3.5 \times 10^7$ cfu/g wet soil to 10 g of the SB soil, 500 μl each of a sterile 10% substrate solution was added (to a final concentration of 5000 ppm). As the substrate, D-cysteine, D-α-alanine, glycine, ethylamine, or pyruvic acid was used. These substances were selected at random from substances that are considered to be metabolites of D-serine in the living body. As a control, 500 μl of sterile water was added to the soil inoculated with the microorganism.

Figure 5:
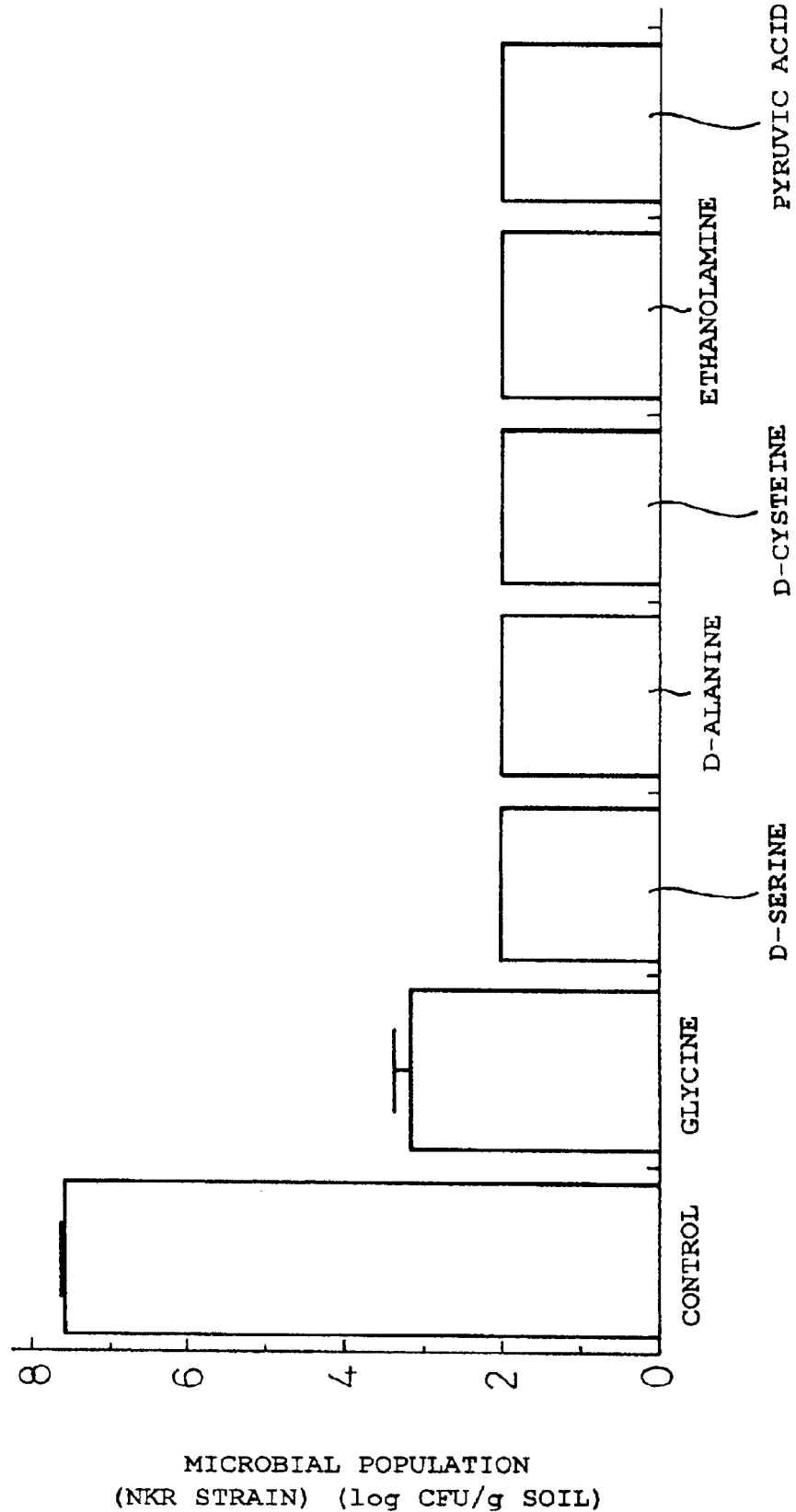
FIG. 5 is a graph showing the controlling effect of D-serine metabolites on the growth of the NKR strain in the soil.

As shown in FIG. 5, by adding these substances, the cell count of the NKR strain declined as compared to the control section, as in the case of D-serine.

In particular, when D-cysteine, D-α-alanine, ethanolamine or pyruvic acid was added, the cell count of the NKR strain markedly declined as compared to the control section, demonstrating the control effect.

From the foregoing, it can be seen that D-serine is very effective in controlling the NKR strain in the soil and that L-serine has almost no effect on controlling the cell count of the NKR strain. Furthermore, as can be seen from Example 7, D-cysteine, D-α-alanine, ethanolamine and pyruvic acid also exhibited control effects as well.

Example 8

After tomato wilt disease bacteria (*Ralstonia solanacearum* OE1-1 strain) was inoculated at $1.6 \times 10^8$ cfu/g wet soil to 10 g of a soil collected from the field of the Aichi-ken Agricultural Research Center, 50 mg of D-serine, D-phenylalanine, myo-inositol, maltose, lactose D(+)-raffinose, or D-sorbitol was added (to a final concentration of 5000 ppm). As a control, a soil to which no microbes were added was used.

Figure 6:
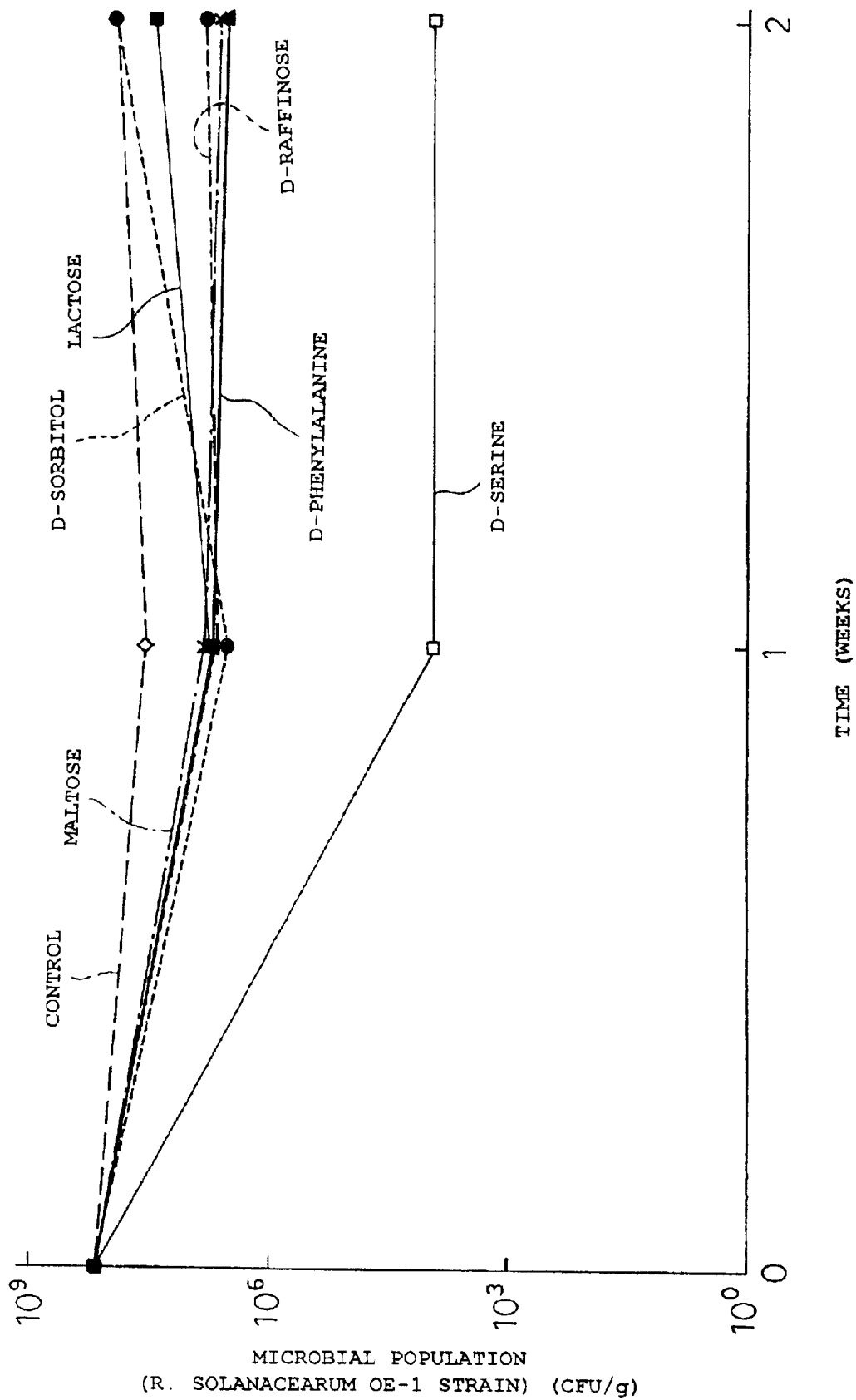
FIG. 6 is a graph showing the controlling effect of D-serine on the growth of *R. solanacearum* OE1-1 strain in the soil.

As shown in FIG. 6, by adding D-serine, the cell count of the OE1-1 strain declined markedly as compared to the control, demonstrating the control effect.

Example 9

Twelve sections of the contaminated soils to which tomato wilt disease bacteria (*Ralstonia solanacearum* OE1-1 strain) was inoculated at $1.6 \times 10^8$ cfu/g wet soil to 10 g of a soil collected from the field of the Aichi-ken Agricultural Research Center were prepared. To five of these test sections, 0 ppm (no addition), 500 ppm, 1000 ppm, 2000 ppm, or 5000 ppm of D-serine was added. To seven of the test sections, 0 ppm (no addition), 500 ppm, 500 ppm×2500 ppm×3100 ppm, 1000 ppm×2, or 1500 ppm of ethanolamine was added. The above 500 ppm×2 means that 500 ppm each of ethanolamine was added on week 0 and week 1. 500 ppm×3 means that 500 ppm each of ethanolamine was added on week 0, 1 and 2.

Figure 7:
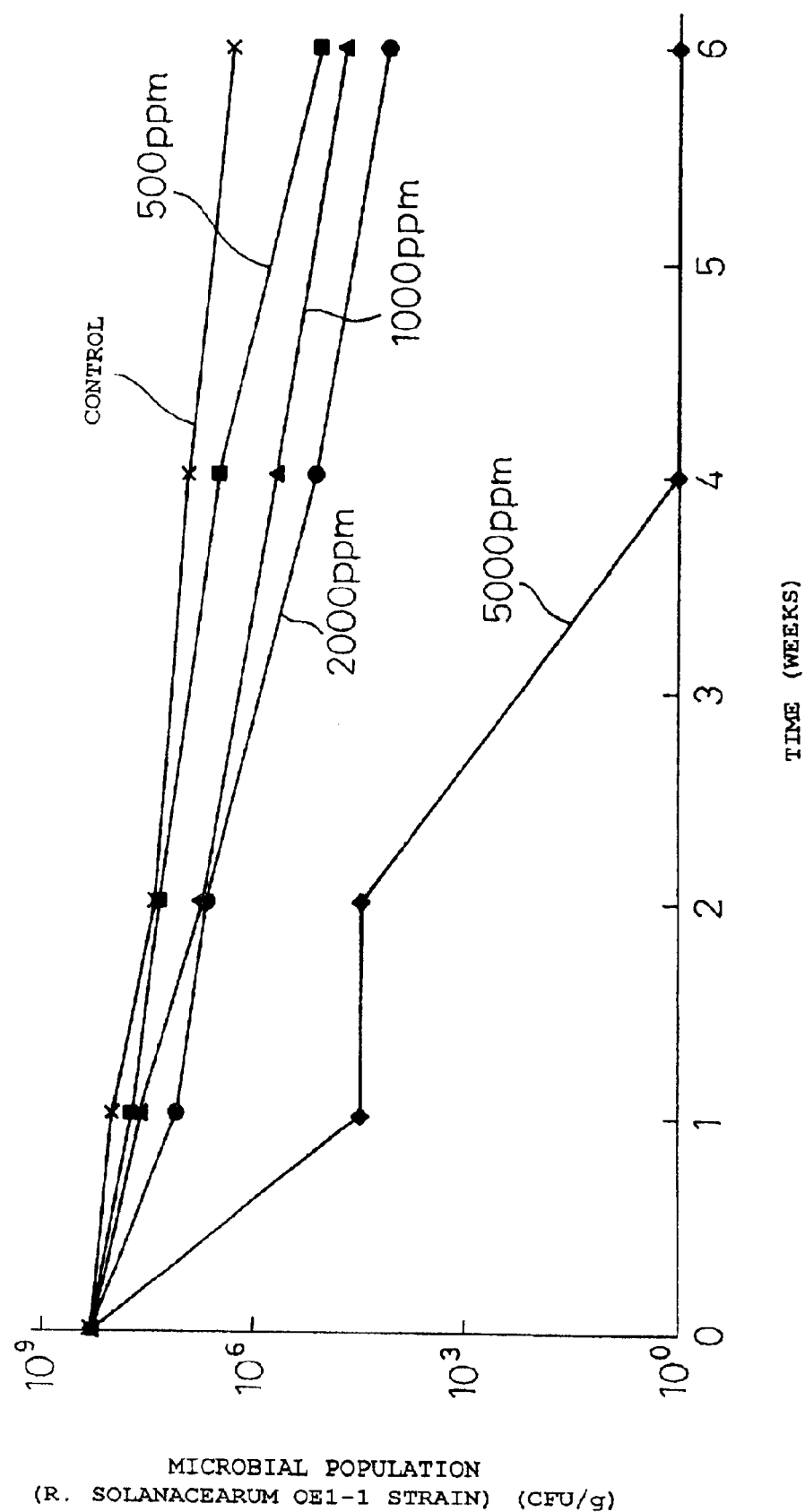
FIG. 7 is a graph showing the controlling effect of D-serine on the growth of *R. solanacearum* OE1-1 strain in the soil.
Figure 8:
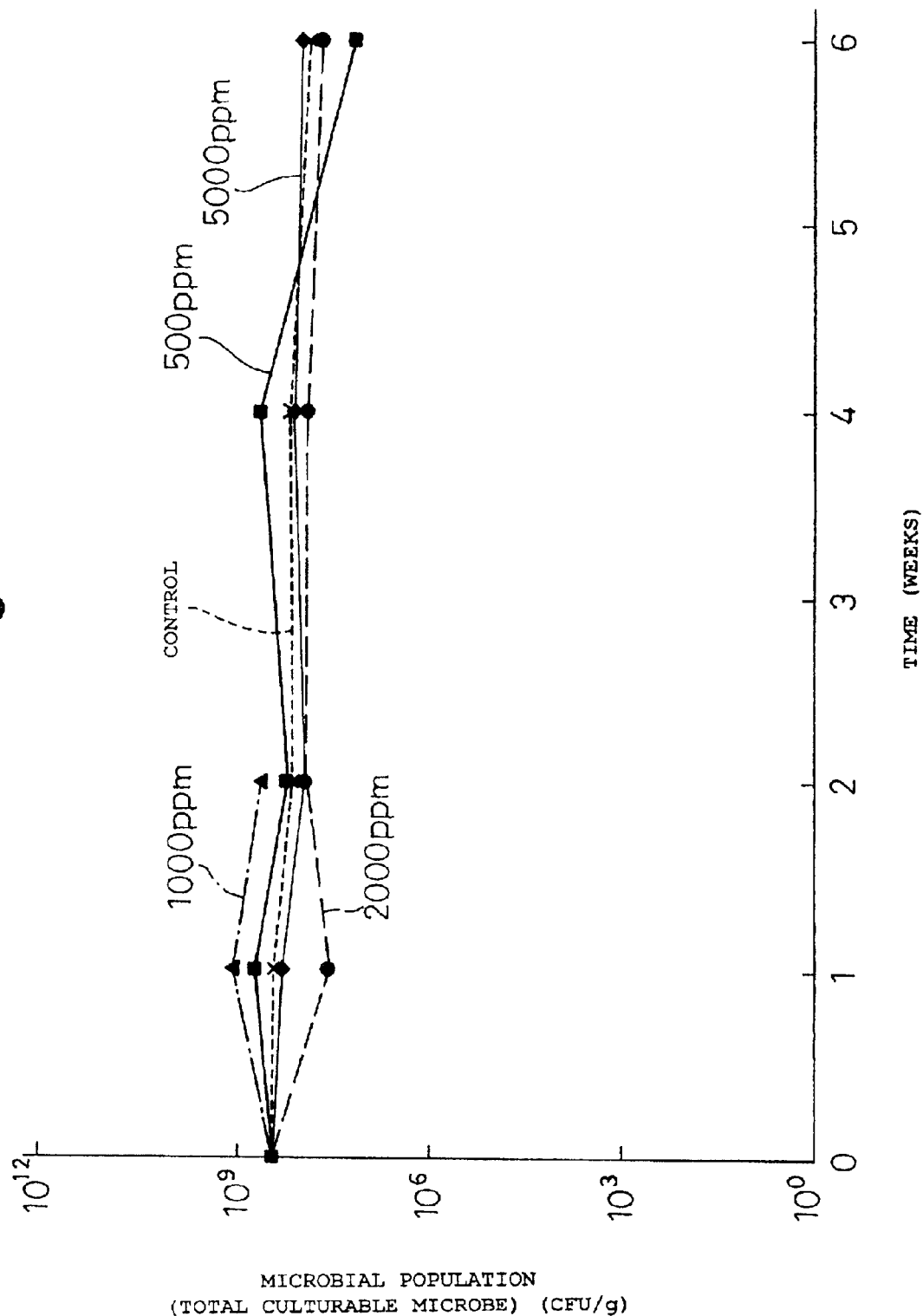
FIG. 8 is a graph showing the total cell count in the soil as measured in the experiment shown in FIG. 7.

As is shown in FIGS. 7 and 8, the addition of D-serine caused a reduction in the cell count of the OE1-1 strain as compared to 0 ppm (control), but almost no changes were observed in the total cell count. This demonstrates that the addition of D-serine specifically controlled *R. solanacearum* OE1-1 strain.

Figure 9:
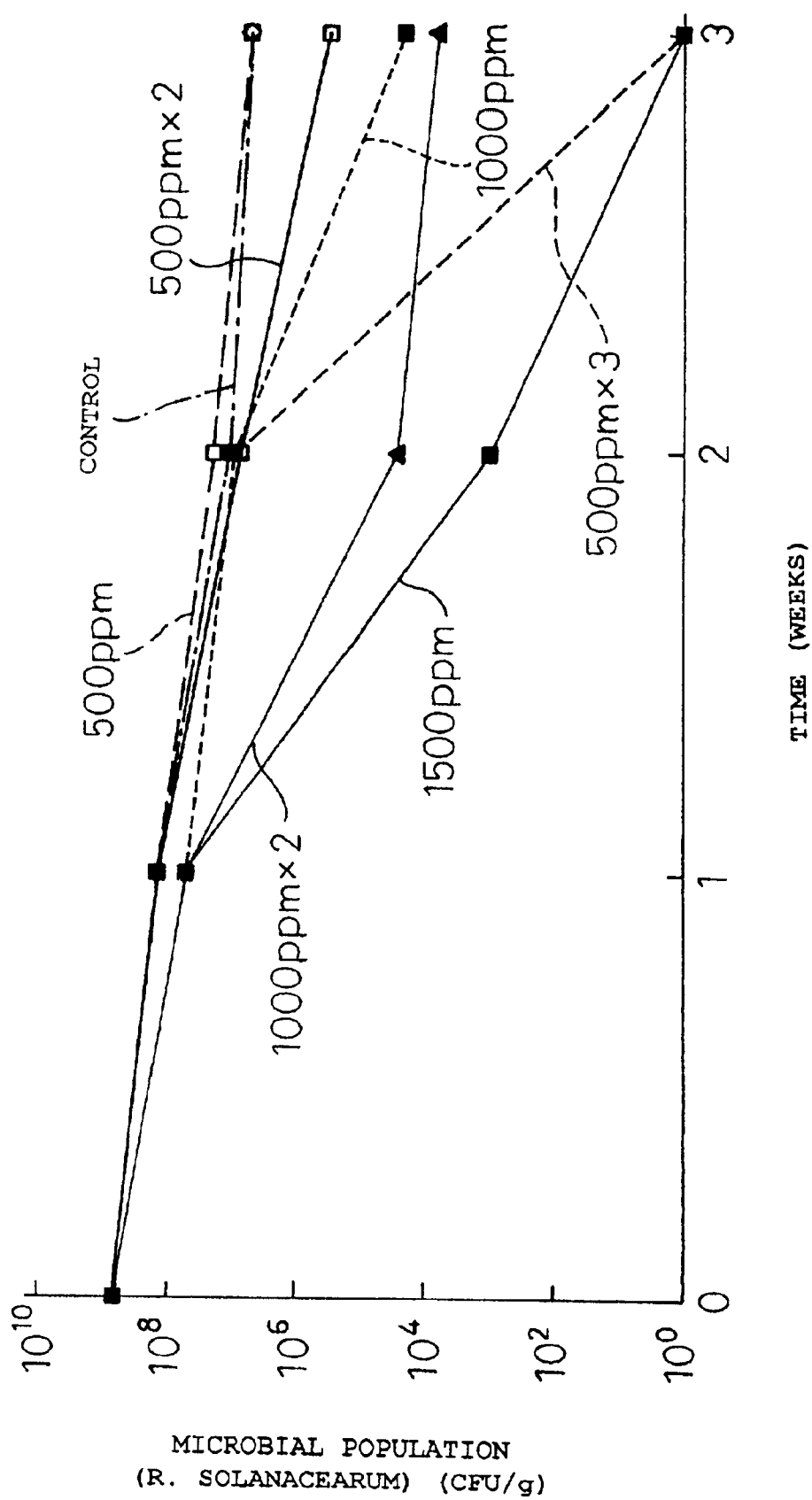
FIG. 9 is a graph showing the controlling effect of ethanolamine on the growth of *R. solanacearum* OE1-1 strain in the soil.
Figure 10:
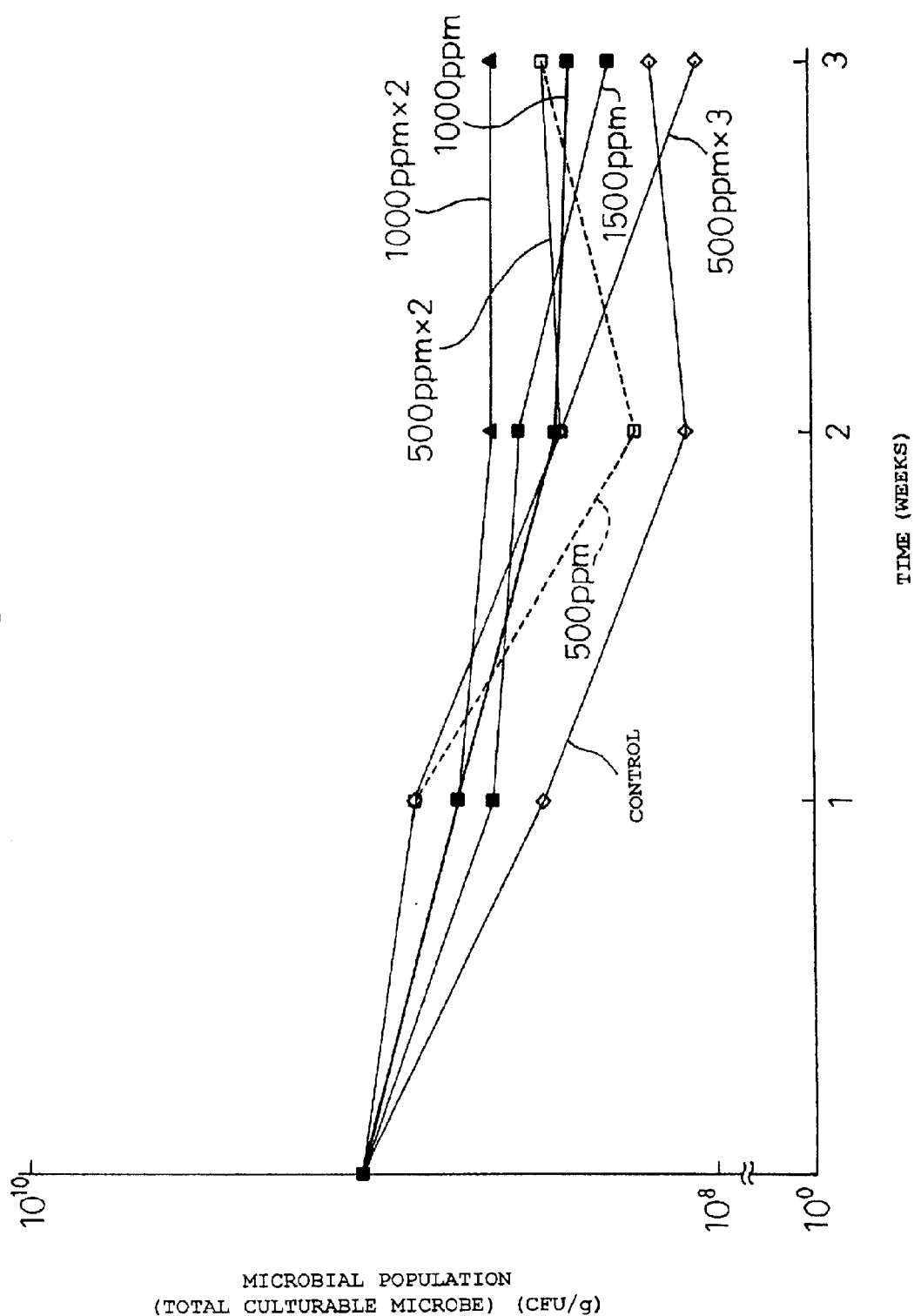
FIG. 10 is a graph showing the total cell count in the soil as measured in the experiment shown in FIG. 9.

Furthermore, as shown in FIGS. 9 and 10, the one-time addition of 500 ppm ethanolamine did not exhibit sufficient effects as compared to 0 ppm, but decrease in the cell counts of the OE1-1 strain was seen when 500 ppm was sequentially added or 1000 ppm or greater was added as compared to 0 ppm. Since the total cell count remained constant in any addition concentration, it is clear that the addition of ethanolamine specifically controlled *R. solanacearum* OE1-1 strain.

Example 10

Figure 11:
FIG. 11 is a photograph showing the state of germination and growth of tomato plants after the addition of various amounts of D-serine to the soil contaminated by *R. solanacearum* OE1-1 strain, in which A represents the result obtained by the addition of 0 ppm of D-serine, B by the addition of 500 ppm of D-serine, C by the addition of 2500 ppm of D-serine, and D by the addition of 5000 ppm of D-serine.

Treatment by D-Serine of the Soil Contaminated by *R. Solanacearum OE*1-1 Strain Four sections each comprising 200 g of the soil contaminated by *R. solanacearum* OE1-1 strain were prepared. To these test sections, 0 ppm (no addition), 500 ppm, 2500 ppm, or 5000 ppm of D-serine was added, and one week later 20 seeds of tomato were sown onto each test soil. On day 4 after the sowing, germination of the tomato seeds was observed in the no D-serine added soil and the 500 ppm D-serine-added soil. On day 6 after the sowing, some young tomato seedlings in the no D-serine added soil started to die, and on day 10 all young seedlings except one in the no D-serine added soil died. In contrast, all young tomato seedlings in the soil to which 500 ppm of D-serine was added grew normally. The result is shown in FIG. 11. In FIG. 11, A represents the result for 0 ppm, B represents 500 ppm, C represents 2500 ppm, and D represents 5000 ppm of D-serine added.

From the above Examples 9 and 10, it is clear that the addition of higher amounts (500 ppm or more) of extrinsic environmental factors such as D-serine and ethanolamine against *R. solanacearum* OE1-1 strain works to control *R. solanacearum* OE1-1 strain, whereas for the development of plants of the solanaceous family the excessive addition of extrinsic environmental factors against *R. solanacearum* OE1-1 strain is not desirable and the range of 500 ppm to 2500 ppm is appropriate.

In Examples of the present invention, tomato was used as an example of solanaceous crops but the invention is useful for plants other than tomato such as eggplant, green pepper, tobacco, potato, and hot pepper.

What is claimed is:

1. A method for indirectly reducing the amount of a target microorganism in soil, wherein the target microorganism is N16-1 strain of *Burkholderia*, comprising the steps of:
   (1) selecting D-serine which is capable of being assimilated by indigenous microbial flora but not by the N16-1 strain of *Burkholderia* and wherein the N16-1 strain of *Burkholderia* and indigenous microbial flora coexist in the soil; and
   (2) adding the D-serine to the soil in an amount effective to cause the growth of the indigenous microbial flora in the soil and to reduce or eliminate the N16-1 strain of *Burkholderia* in the soil.

2. The method according to claim 1, wherein the soil to which the D-serine is added is after bioremediation, and the N16-1 strain of *Burkholderia* is a microorganism which decomposes a contaminant in the soil.

3. The method according to claim 2, wherein the N16-1 strain of *Burkholderia* is a microorganism which decomposes a chlorine-containing organic compound.

* * * * *